United States Patent [19]

Patil

[11] Patent Number: 4,879,307

[45] Date of Patent: Nov. 7, 1989

[54] DIOXOLANE ANTIBACTERIAL COMPOSITIONS

[75] Inventor: Ashok D. Patil, King of Prussia, Pa.

[73] Assignee: Harbor Branch Oceanographic Institution, Inc., Ft. Pierce, Fla.

[21] Appl. No.: 230,036

[22] Filed: Aug. 9, 1988

Related U.S. Application Data

[63] Continuation-in-part of Ser. No. 107,164, Oct. 13, 1987, abandoned, which is a continuation-in-part of Ser. No. 825,061, Feb. 4, 1986, abandoned.

[51] Int. Cl.$^4$ .................. A61K 31/335; C07D 317/04
[52] U.S. Cl. ...................................... 514/467; 549/454
[58] Field of Search ........................ 549/454; 514/467

[56] References Cited

PUBLICATIONS

Phillipson et al., JACS, 105, 7735 (1983).

Primary Examiner—Nicky Chan
Attorney, Agent, or Firm—Carroll F. Palmer

[57] ABSTRACT

The invention comprises antitumor compounds of the formula:

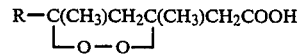

wherein R is an alkyl group of up to 20 carbon atoms.

4 Claims, No Drawings

DIOXOLANE ANTIBACTERIAL COMPOSITIONS

REFERENCE TO RELATED APPLICATIONS

This application is a continuation-in-part of Ser. No. 107,164, filed Oct. 13, 1987, which, in turn, is a continuation-in-part of Ser. No. 825,061, filed Feb. 4, 1986; now abandoned.

FIELD OF THE INVENTION

This invention relates to new dioxolane organic compounds which have useful antibacterial, antifungal and antitumor activity. More particularly, this invention relates to new dioxolane compositions derived from marine organisms, i.e., maring sponge of the family Halichondriidae.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia, which term refers to the symptomatic discomfort that accompanies the infliction of a mammal with a tumor. These symptoms include weakened condition of the inflicted mammal as evidenced by, for example, weight loss. The seriousness of cancer is well known. Cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Bacteria are of practical importance to man. While some bacteria are useful in industry and for soil fertilization, others are harmful. Bacteria are responsible for diseases in man, other animals and plants including, for example in man botulism, diphtheria, tetanus and tuberculosis. Bacteria also cause large economic damage due to spoiling of various foods (e.g., milk products).

While many methods and chemical compositions have been utilized in controlling bacteria caused disease and other maladies, new antibacterial methods and chemical compositions are needed.

Prevention of the growth of fungus and the infections and maladies caused by fungus to mammals and plants are also of importance to man. The presence of fungi may cause various diseases and infections in man including mycotic disease (e.g., pulmonary candidiasis and pulmonary blastomycosis.) Certain yeastlike organisms (e.g. *cryptococcus neoformans*) may cause serious infections of the central nervous system. More commonly known fungal infections in humans and mammals include ringworm (fungus infections of hair and nail areas), as well as, resistant infections of the skin. Many other fungal infections inflict humans and mammals in the areas of skin, mucous membranes, intestinal tract, vaginal area and lungs.

Plants are also attacked by various fungi. Agricultural damage caused by fungus infections amounts to billions of dollars annually. Various inorganic and organic fungistats and fungicides have been tried with limited success. It is of course important for the fungistat or fungicide to kill the fungi but not the plant and to leave no toxic residue on the edible part of the plant. Various methods have been utilized to combat fungus infection in agriculture including the foliage fungicide method by which plants are coated with a preventive weather-resistant fungicide. Seed treatment and soil treatment methods require fungicides that are safe for seeds and resist degradation by soil and soil microorganisms. Chemotherapeutants are fungicides which permeate the plant to protect new growth or eliminate infections which have already occurred within the plant. Agricultural fungistats and fungicides and their application must also meet very stringent requirements and regulations, which have been promulgated, for example, in the United States.

Considerable research and resources have been devoted to combating fungal infections in both mammals and plants. While some antifungal agents and methods have been developed that inhibit the spread of fungus and fungus-caused diseases in both mammals and plants and treat infected mammals and plants new methods and antifungal chemical compositions are needed.

It has now been found that certain organic compounds derived from extracts of a marine sponge, of the family Halichondriidae, possess useful antitumor, antibacterial and antifungal activity.

SUMMARY OF THE INVENTION

It is therefore an object of the invention to provide novel compositions which are useful as antitumor, antibacterial and antifungal agents; methods of antitumor, antibacterial and antifungal use of such compositions; and a process for producing the novel compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the general formula I:

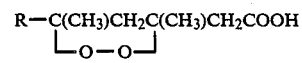

wherein R is an alkyl group of up to 20 carbon atoms.

In preferred embodiments of the invention, the composition is substantially pure and R is an alkyl group of from 13 to 17 carbon atoms. In more preferred embodiments of the invention, the invention comprises compositions of the formulae (1–5):

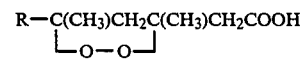

wherein R is

1: R = n C₁₃H₂₇
2: R = n C₁₄H₂₉
3: R = n C₁₅H₃₁
4: R = n C₁₆H₃₃
5: R = n C₁₇H₃₅

As embodied and fully described herein, the invention also comprises antitumor, antibacterial, and antifungal compositions comprising, as active ingredient, an effective antitumor, antibacterial and antifungal amount, respectively, of one or more compositions according to formulae I and 1–5 and a non-toxic pharmaceutically acceptable carrier or diluent.

As embodied and fully described herein, the invention also comprises a process to produce the compounds of formulae I and 1–5. The process comprises the steps of collecting marine sponge, of the family Halichondriidae; contacting the sponge with a suitable organic solvent; obtaining an extract thereof; and isolating a compound according to formula I from the extract.

In preferred embodiments of the invention the suitable organic solvent is selected from the group consisting of methanol, hexane, methylene chloride, acetone, methyl ethyl ketone, ethyl acetate, ethanol, and methyl isobutyl ketone.

As embodied and fully described herein, the invention further comprises a method for inhibiting tumors in a host and a therapeutic method for treating cancerous cachexia comprising contacting a tumor with an effective antitumor amount of one or more compositions of formulae I and 1–5.

As embodied and fully described herein, the invention further comprises a method for inhibiting the growth of bacteria comprising contacting bacteria with an effective antibacterial amount of one or more compositions of formulae I and 1–5.

As embodied and fully described herein, the invention further comprises a method for inhibiting the growth of fungus comprising contacting fungus with an effective antifungal amount of one or more compositions of formulae I and 1–5.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formula (I):

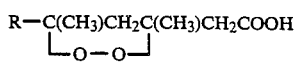

wherein R is an alkyl group of from 1 to 20 carbon atoms.

In preferred embodiments of the invention, the composition is substantially pure and R is an alkyl group of 13 to 17 carbon atoms. In more preferred embodiments of the invention, the invention comprises compositions of the formulae (1–5):

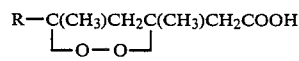

wherein R is

1: R = n C₁₃H₂₇
2: R = n C₁₄H₂₉
3: R = n C₁₅H₃₁
4: R = n C₁₆H₃₃
5: R = n C₁₇H₃₅

In accordance with the invention, an antitumor composition is provided comprising as active ingredient an effective antitumor amount of one or more of the compositions described above and identified by formulae I and 1–5 in a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor formulae I and 1–5. The effectiveness of the compositions of the invention for inhibiting tumors indicates their usefulness for controlling tumors in hosts including mammals and for treating cancerous cachexia.

In accordance with the invention, an antibacterial composition is provided comprising as active ingredient an effective antibacterial amount of one or more of the compositions described above and identified by formulae I and 1–5 in non-toxic pharmaceutical acceptable carrier or diluent. While effective amounts may vary, as conditions in which the antibacterial compositions are used vary, a minimal dosage required for activity is generally between 5 and 25 micrograms or less against *Bacillus subtilis* bacteria showing a zone of inhibition of at least 8 mm. Useful examples of non-toxic pharmaceutically acceptable carriers or diluents include, but are not limited to, the following: ethanol, dimethyl sulfoxide and glycerol.

In accordance with the invention, a method for inhibiting bacteria in a host is provided comprising contacting bacteria with an antibacterial amount of one or more compositions according to formulae I and 1–5. The effectiveness of the compositions of the invention for inhibiting bacteria indicates their usefulness for controlling bacteria and bacterial related diseases in hosts including mammals. Further, such compositions may be utilized to prevent or retard spoilage of food due to the presence and growth of bacteria.

In accordance with the invention, an antifungal composition is provided comprising as active ingredient an effective antifungal amount of one or more of the compositions described above and identified by formulae I and 1–5 in a non-toxic pharmaceutically acceptable carrier or diluent. While effective amounts may vary, as conditions in which the antifungal compositions are used vary, a minimal dosage required for activity is generally 1.0 or less micrograms against Saccharomyces, cerevisiae fungi showing a zone of inhibition of growth of at least 8mm. Useful examples of non-toxic pharmaceutically acceptable carriers or diluents include, but are not limited to, the following: ethanol, dimethyl sulfoxide and glycerol.

In accordance with the invention, a method for inhibiting fungus in a host is provided comprising contacting fungus with an antifungal amount of one or more compositions according to formulae I and 1-5. The effectiveness of the compositions of the invention for inhibiting fungus indicates their usefulness for controlling fungus and fungus related diseases in hosts including mammals. Further, such compositions may be useful as agricultural fungicides.

In accordance with the invention, a process to produce a compound according to formulae I and 1-5 comprises the step of: collecting marine sponge of the family *Halichondriidae*; contacting the collected sponge with a suitable organic solvent; obtaining an extract of the solvent and sponge mixture; and isolating a compound according to formula I.

A detailed description and explanation of a preferred embodiment of the process of the invention to produce the compound according to formulae I and 1-5 is as follows: marine sponge of the family *Halichondriidae*, is collected from rock surfaces in the Bahamas off Chubb Cay at a depth of 2,500 feet. The sponge is contacted with methanol (a first solvent) in a mortar or blender. The methanol extract is concentrated and triturated with hexane (a second solvent) and methylene chloride (a third solvent) to give an organic residue. The residue is grossly separated into fractions which yield various compositions. Treatment with ethereal diazomethane yields a fraction containing two methyl esters. The ester fraction then is hydrolyzed with 5% aqueous alcoholic potassium hydroxide. Compositions according to the invention are isolated by various chromatographic techniques from the fractions obtained.

While methanol, hexane and methylene chloride are the presently preferred choices for the first, second and third solvents, respectively, other suitable solvents may be substituted. A suitable first solvent should be capable of extracting a compound according to any one of formulae I and 1-5 from other components of the sponge. Suitable first solvents which may be substituted for methanol include, but are not limited to, the following organic solvents: methyl ethyl ketone; ethyl acetate; ethanol; acetone; and methyl isobutyl ketone. Suitable second and third solvents should be capable of triturating and separating into various fractions the various compounds of formulae I and 1-5 from other components that may be present in the first solvent extract. Suitable second and third solvents, which may be substituted for either hexane or methylene chloride or both, include, but are not limited to, either hexane or methylene chloride alone or the following organic solvents: chloroform; trichloroethylene; and lower substituted benzenes Different ratios of first, second and third solvents and any combination may be used in the invention as would be known to those skilled in the art.

Any suitable fractionation and isolation techniques may be utilized in accordance with the process of the invention. Suitable fractionation techniques include various chromatographic techniques such as high-performance liquid chromatography (HPLC) with a suitable column as would be known to those skilled in the art [e.g., a Whatman partisil column (M9 50/9.4]eluted with a suitable solvent [e.g., methanol: 0.01N Sodium acetate, 85:15].

It is therefore apparent that the compositions of the invention, the processes for producing the compositions of the invention and the methods for utilizing the compositions of the invention to inhibit tumors, bacteria and fungus growth are effective for inhibiting or destroying tumors, fungus and bacteria and controlling diseases caused thereby in fulfillment of the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention The starting materials and reagents in the examples whose method of preparation are not indicated are commercially available from sources known to the art such as chemical supply houses.

Examples 1-5

Preparation of 1,2-dioxolane-3-acetic acids with n-alkyl side chains (1-5):

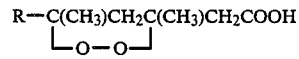

1: R = n-$C_{13}H_{27}$
2: R = n-$C_{14}H_{29}$
3: R = n-$C_{15}H_{31}$
4: R = n-$C_{16}H_{33}$
5: R = n-$C_{17}H_{35}$

Marine sponge of the family *Hydrachondriidae*, was collected from rock surfaces in water at a depth of 2,500 feet off Chubb Cay in the Bahamas. The sponge was frozen. 250 grams of the frozen sponge was admixed with 1500 ml. of methanol and furnished a yellow residue. The yellow residue was triturated with 500 ml. of hexane and 500 ml. of methylene chloride. The methylene chloride extract was fractioned employing silica gel column chromatography (E. Merck, Kieselgel-60, 230-400 mesh; $CH_2Cl_2$:MeOH mixtures) followed by preparation thin layer chromatography (E. Merck, 70:30, ethyl ether: petroleum ether, 7:93, MeOH:$CH_2Cl_2$) which furnished a bio-active fraction which after treatment with 5 ml. of ethereal diazomethane yielded two methyl esters, which were separated by silica gel HPLC. Hydrolysis of the active ester with 5% aqueous alcoholic potassium hydroxide followed by HPLC (ODS-3 Whatman, 85:15, MeOH:0.01 N NaOAc) provided the five epidioxy saturated long chain acids (1-5) as colorless liquids.

These epidioxy acids inhibit the growth of tumor cells in vitro bioassays and show substantial antibacterial and antifungal activity in disc diffusion assays.

ANTITUMOR ACTIVITIES OF THE COMPOUNDS OF THE INVENTION

The following assay method was utilized to illustrate the antitumor effectiveness of the compositions of Formula I, and particularly compositions 3 and 4 of the examples.

P388 MOUSE LEUKEMIA CELL CYTOTOXICITY ASSAY 24-WELL PLATE SCREENING ASSAY AND TUBE ASSAY PROTOCOL

MATERIALS UTILIZED

Media - Dulbeccos with glucose and pyruvate (Biologos, Inc) with 10% horse serum, (Biologos, Inc) and 1.0 µg/ml gentamicin (Gibco).
Cells - P388 mouse leukemia cells and HCT-8 human colon cells (American Type Culture Collection) in media at a concentration of $5 \times 10^4$ cells/ml. Sterile 24-well culture plates (Nunc) for screening or $12 \times 75$ mm glass culture tubes (Becton-Dickinson) for tube assay. Microdispenser with 1 to 5 µl increments (Drummond Scientific Co. Broomall PA).
Finnpipette with 5 to 50 µl increments and Finnpipette with 50 to 200 µl increments.

PROCEDURE for P388 Assay

1. A sample of the composition to be assayed is added to each well or tube in an amount of from 200 ug/ml and 100 ug/ml for screening. For DDC of known active compounds use log concentrations from 100 ug/ml to 0.01 ug/ml for range-finding assay; when range has been determined, use five concentrations between highest and lowest active concentrations.
2. Add 2.0ml of $5 \times 10^4$ cell suspension in media to each well or tube. Tubes are loosely covered with parafilm.
3. Incubate in 5% $CO_2$ incubator for 48 hours.
4. Visually read plates with inverted microscope, comparing with solvent control. Assign activity as follows:

0=90-100% of control growth
1+ =75-89% of control growth
2+ =50-74% of control growth
3+ =25-49% of control growth
4+ =25% of control growth Repeat all positive samples using tube assay.
5. For Tube assays—Mix tube well on vortex and remove 0.5 ml aliquot and add to 9.5 ml nf diluent fluid (Isoton - Coulter) in Accuvette (Coulter) and mix well by inversion immediately before counting, taking care not to produce excessive bubbles. Count on Coulter Counter (Counter is set to count 0.5 ml of the solution; therefore counts may be converted to cll/ml in original assay tube by multiplying count by 40.

Positive control - Vinblastine or Vincristine in aqueous solution.

Final Conc. of Vinblastine or Vincristine control (use 2µl assay)

Procedure for HCT-8 cells

Same as for P388 except substitute the following for steps 2-3:

2* Seed/ml cell of HCT-8 ($5 \times 10^3$) Cell suspension in media to each well or tube.
Tubes are loosely covered with parafilm.
3* Incubate in 5% $CO_2$ incubator for 48 hours.

3a* Add 2 ul extract 100 µg) to each well and incubate for an additional 120 hours.
3b* Discard medium and stain with methylene blue.

Concentration

| Solution Conc. | Concentration Amt added | Final conc. in test |
|---|---|---|
| 10 mg/ml | 2 µl | 10 µg/ml |
| 5 mg/ml | 2 µl | 1 µg/ml |
| 0.5 mg/ml | 2 µl | 0.5 µg/ml |
| 0.1 mg/ml | 2 µl | 0.1 µg/ml |

Notes

For solvents other than water, allow solvent to evaporate from tube or well in hood.

Chloroform and butanol cannot be used in the plastic 24—well plates—use glass tubes.

Always run a solvent control in duplicate in the last two wells of each plate or four tubes for each rack of 72 or less tubes. Also run four wells or tubes with media and cells only per run of plates or tubes. When using volumes of aqueous solutions greater than 200 µl, dry sample and bring up to desired concentration in media.

TABLE 1

| Composition Example | Antitumor Assay Results | | |
|---|---|---|---|
| | Concentration | P388 | HCT-8 |
| 3 | 10 µg/ml | 4+ | 4+ |
| | 5 | 4+ | 4+ |
| | 0.5 | 4+ | 4+ |
| 4 | 10 | 4+ | 4+ |
| | 5 | 4+ | 4+ |
| | 0.5 | 4+ | 2+ |

ANTIMICROBIAL AND ANTIFUNGAL ASSAY PROTOCOL

Extracts were screened against bacterium *Bacillus subtilis* and fungus *Saccharomyces Cerevisiae* using pre-seeded 85-mm petri dishes. Bioassay discs (6-mm) were loaded with 40 microliters of test sample, air dried and applied to the plates. These were incubated at 35° C. for 18 h and the diameters of the inhibition zones were recorded Acids 1-5 show 20-mm zone of inhibition at a concentration of 25 ug/disc vs. *Bacillus subtilis* and a 32mm zone of inhibition at 10 ug/disc vs. *Saccharomyces cerevisiae*. These zones of inhibition at the reported concentration of acids 1-5 show that these acids are effective for inhibiting the growth of bacteria and fungi.

The scope of the present invention is not limited by the description, examples, and suggested uses herein and modifications can be made without departing from the spirit of the invention. For example, it may be noted that other derivatives of the compositions of examples 1-5 such as an ester or fluorinated derivative may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the

What is claimed is:

1. A compound of the formula:

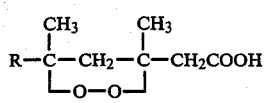

wherein R is a n-alkyl group $C_{13}H_{27}$, $C_{14}H_{29}$, $C_{15}H_{31}$, $C_{16}H_{33}$, or $C_{17}H_{35}$.

2. A compound of claim 1 that is substantially pure.

3. A pharmaceutical composition comprising, as an active ingredient, an effective antibacterial amount of one or more of the compounds of claim 1 and a non-toxic pharmaceutically acceptable carrier or diluent.

4. A pharmaceutical composition comprising, as an active ingredient, an effective antibacterial amount of one or more of the compounds of claim 2 and a non-toxic pharmaceutically acceptable carrier or diluent.